(12) United States Patent
Addington et al.

(10) Patent No.: US 9,470,641 B1
(45) Date of Patent: Oct. 18, 2016

(54) SYSTEM AND METHOD FOR MEASURING REFLECTED OPTICAL DISTORTION IN CONTOURED GLASS SHEETS

(71) Applicant: GLASSTECH, INC., Perrysburg, OH (US)

(72) Inventors: Jason C. Addington, Sylvania, OH (US); Michael J. Vild, Toledo, OH (US); Benjamin L. Moran, Perrysburg, OH (US)

(73) Assignee: Glasstech, Inc., Perrysburg, OH (US)

( * ) Notice: Subject to any disclaimer, the term of this patent is extended or adjusted under 35 U.S.C. 154(b) by 0 days.

(21) Appl. No.: 14/752,033

(22) Filed: Jun. 26, 2015

(51) Int. Cl.
| | |
|---|---|
| C03B 11/08 | (2006.01) |
| G01N 21/958 | (2006.01) |
| G01N 21/89 | (2006.01) |
| C03B 23/00 | (2006.01) |
| G01N 21/84 | (2006.01) |

(52) U.S. Cl.
CPC ............. *G01N 21/958* (2013.01); *C03B 23/00* (2013.01); *G01N 21/8903* (2013.01); *G01N 2021/845* (2013.01)

(58) Field of Classification Search
CPC .......................... G01H 21/1958; C03B 11/08
USPC ................................................ 65/158, 29.12
See application file for complete search history.

(56) References Cited

U.S. PATENT DOCUMENTS

| | | |
|---|---|---|
| 4,585,343 A | 4/1986 | Schave et al. |
| 4,629,319 A | 12/1986 | Clarke et al. |
| 4,989,984 A | 2/1991 | Salinger |
| 5,705,805 A | 1/1998 | Han |
| 6,031,221 A | 2/2000 | Furnas |
| 6,100,990 A | 8/2000 | Ladewski |
| 6,392,754 B1 | 5/2002 | Pingel et al. |
| 6,512,239 B1 | 1/2003 | Weiss et al. |
| 7,345,698 B2 | 3/2008 | Abbott et al. |
| 7,430,049 B2 | 9/2008 | Bertin-Mourot et al. |
| 7,471,383 B2 | 12/2008 | Ehrick |
| 8,049,879 B2 | 11/2011 | Shetterly et al. |
| 8,064,069 B2 | 11/2011 | Wienand et al. |

(Continued)

FOREIGN PATENT DOCUMENTS

| | | |
|---|---|---|
| DE | 10127304 A1 | 12/2002 |
| FR | 2975776 A1 | 11/2012 |
| WO | 2009102490 A1 | 8/2009 |

OTHER PUBLICATIONS

International Search Report and Written Opinion from related PCT Application No. PCT/US2016/032837, dated Aug. 18, 2016.

(Continued)

*Primary Examiner* — Mark Halpern
(74) *Attorney, Agent, or Firm* — Brooks Kushman P.C.

(57) ABSTRACT

A system for measuring optical distortion in a contoured glass sheet includes a conveyor for conveying the glass sheet in a first direction, at least one display projecting a preselected multi-phase non-repeating contrasting pattern, and at least one camera, each one of the cameras uniquely paired with one of the displays. The system may also include a control programmed to execute logic for controlling each of the cameras to acquire the desired images, and logic for analyzing and combining the data acquired by the cameras to construct a definition of the surface of the glass sheet, and logic for performing one or more optical processing operations on the surface data to analyze the optical characteristics of the glass sheet.

22 Claims, 7 Drawing Sheets

(56) References Cited

U.S. PATENT DOCUMENTS

| | | |
|---|---|---|
| 8,284,396 B2 | 10/2012 | Rudert |
| 8,670,031 B2 | 3/2014 | Case et al. |
| 2003/0030639 A1 | 2/2003 | Ritter |
| 2003/0053066 A1* | 3/2003 | Redner ................. G01N 21/57 356/448 |
| 2004/0057046 A1* | 3/2004 | Abbott ................ G01N 21/896 356/239.1 |
| 2006/0028096 A1* | 2/2006 | Kushibiki .............. G01N 25/16 310/319 |
| 2006/0050284 A1 | 3/2006 | Bertin-Mourot et al. |
| 2006/0182308 A1 | 8/2006 | Gerlach et al. |
| 2008/0050008 A1 | 2/2008 | Oaki |
| 2008/0144044 A1 | 6/2008 | Ehrick |
| 2008/0247668 A1 | 10/2008 | Li et al. |
| 2008/0310701 A1* | 12/2008 | Caroli ................... G01B 11/25 382/141 |
| 2009/0238449 A1 | 9/2009 | Zhang et al. |
| 2009/0257052 A1 | 10/2009 | Surrell |
| 2009/0282871 A1* | 11/2009 | Shetterly ............. G01N 21/958 65/29.12 |
| 2010/0051834 A1 | 3/2010 | Lopatin |
| 2010/0060905 A1 | 3/2010 | Wienand |
| 2010/0149327 A1 | 6/2010 | Okamura |
| 2010/0260378 A1 | 10/2010 | Noy et al. |
| 2010/0309328 A1* | 12/2010 | Ehrick ............... G01B 11/2509 348/222.1 |
| 2010/0315635 A1* | 12/2010 | Janzen ................ G01N 21/474 356/326 |
| 2011/0187855 A1 | 8/2011 | Pichon et al. |
| 2011/0285987 A1 | 11/2011 | Surrell |
| 2011/0320023 A1 | 12/2011 | Sullivan et al. |
| 2012/0098959 A1* | 4/2012 | Addington ........... G01N 21/958 348/125 |
| 2012/0229682 A1 | 9/2012 | Ng et al. |
| 2012/0269404 A1 | 10/2012 | Hassebrook et al. |
| 2013/0088630 A1 | 4/2013 | Kanade et al. |
| 2014/0253929 A1 | 9/2014 | Huang et al. |

OTHER PUBLICATIONS

International Search Report and Written Opinion from related PCT Application No. PCT/US2016/032846, dated Aug. 18, 2016.
International Search Report and Written Opinion from related PCT Application No. PCT/US2016/032848, dated Aug. 17, 2016.
International Search Report and Written Opinion from related PCT Application No. PCT/US2016/032855, dated Aug. 18, 2016.
International Search Report and Written Opinion from related PCT Application No. PCT/US2016/032851, dated Aug. 25, 2016.
International Search Report and Written Opinion from related PCT Application No. PCT/US2016/032840, dated Aug. 30, 2016.

* cited by examiner

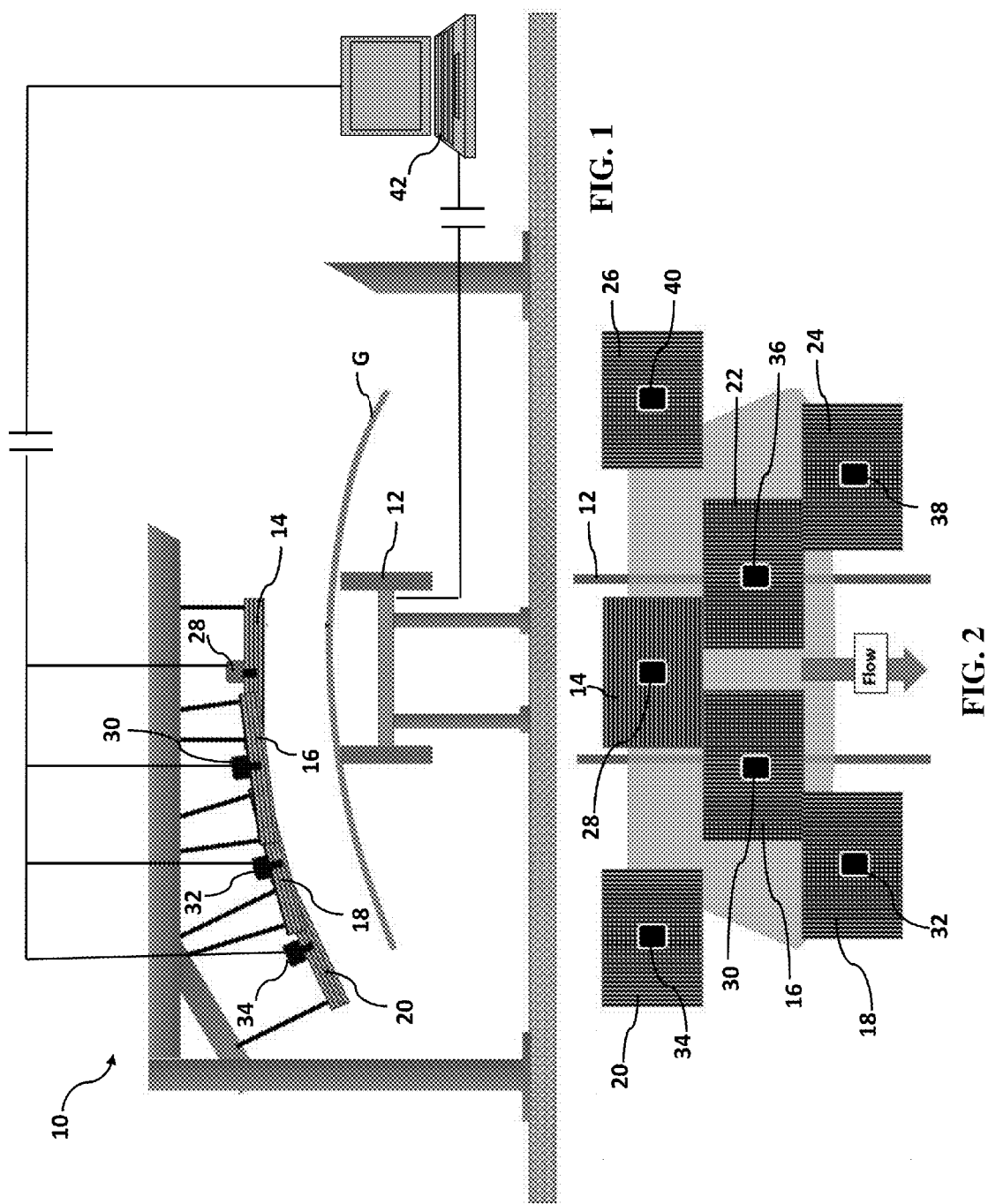

SYSTEM AND METHOD FOR MEASURING REFLECTED OPTICAL DISTORTION IN CONTOURED GLASS SHEETS

TECHNICAL FIELD

This invention relates to a method and apparatus for measuring reflected optical distortion in glass sheets.

BACKGROUND

Manufacturers of glass sheets, particularly glass sheets formed into various curved shapes for use as automotive windshields, backlites, and sidelites, are interested in measuring and evaluating the amount of optical distortion in the formed sheets that might be perceived by a human observer, such as the operator or passenger in a vehicle in which the glass may be mounted as the windshield, backlite, or sidelite.

Various types of glass sheet optical inspection systems are known. One known optical inspection system is disclosed in United States Application Publication No. 2012/0098959 A1, which application is also assigned to the assignee of the invention disclosed herein. This disclosed optical inspection system acquires images of a pre-defined, contrasting pattern transmitted through the glass sheet, and may be implemented in either a laboratory (i.e., off-line) or an in-line configuration in which the inspection system is mounted to inspect glass sheets as they are being conveyed in a processing system, such as, for example, a glass sheet heating, bending and cooling system.

The optical characteristics of a glass sheet may also be measured by acquiring and analyzing image data corresponding to the image of a pre-defined, contrasting pattern that is reflected from one of the surfaces of the glass sheet. Thus, it is desirous for at least this purpose to develop a system and method for quickly acquiring data corresponding to the surface of a glass sheet and analyzing the acquired surface data to assess and report on the optical characteristics of the glass sheet, particularly as the glass sheet is being transported on a conveyor between or after bending, cooling, or other processing operations.

SUMMARY

The disclosed system and method for measuring optical distortion in a contoured glass sheet includes, as components, (1) a system and method for acquiring three-dimensional surface data corresponding to the glass sheet, and (2) a system and method for receiving the acquired surface data and performing one or more optical processing operations to analyze the optical characteristics of the glass sheet.

The surface data acquisition system may include a conveyor for conveying the glass sheet in a first direction generally parallel to the first dimension of the glass sheet, at least one display projecting a preselected contrasting pattern, and at least one camera, each one of the cameras uniquely paired with one of the displays, wherein each display and camera pair are mounted in a spaced-apart relationship a known distance and angle from the surface of the glass sheet such that the camera detects the reflected image of the pattern projected on the surface of the glass sheet from its associated display.

The surface data acquisition system may, in one embodiment, include two or more cameras, each one of the cameras being uniquely paired with one of the displays as described above, wherein each of the display and camera pairs are spaced apart from each other at least in a second direction across the second dimension of the glass sheet such that each camera detects the reflected image of the pattern projected on the surface of the glass sheet from only its associated display, and wherein the patterns detected by the two or more cameras together cover the entire surface in the direction of the second dimension of the glass sheet.

The surface data acquisition system may also include a programmable control including at least one processor programmed to execute logic for controlling each of the cameras to acquire at least one image of the reflected pattern of the associated display on the glass sheet as the glass sheet is conveyed across the path of the projected pattern in the first direction, and logic for analyzing and combining the data acquired by the two or more cameras to construct surface data representative of the surface of the glass sheet.

The disclosed optical processing system may include at least one processor including logic for receiving the captured image data and performing one or more optical processing operations to analyze the optical characteristics of the glass sheet and display or otherwise report selected information associated with the analysis.

The system for measuring optical distortion may utilize a single computer which controls the conveyor and the operation of the cameras, and includes the previously described surface data acquisition logic, as well as the optical distortion processing logic. Alternatively, the conveyor control, camera controls, surface data acquisition and optical processing may be integrated but implemented on separate or multiple processors, in one or more programmable logic controllers and/or computers.

BRIEF DESCRIPTION OF THE DRAWINGS

FIG. 1 is a schematic partial end view of one embodiment of the disclosed glass sheet optical inspection system showing four of the seven screens utilized in this embodiment;

FIG. 2 is a schematic top view of the disclosed glass sheet optical inspection system of FIG. 1;

DETAILED DESCRIPTION

Figure 3:
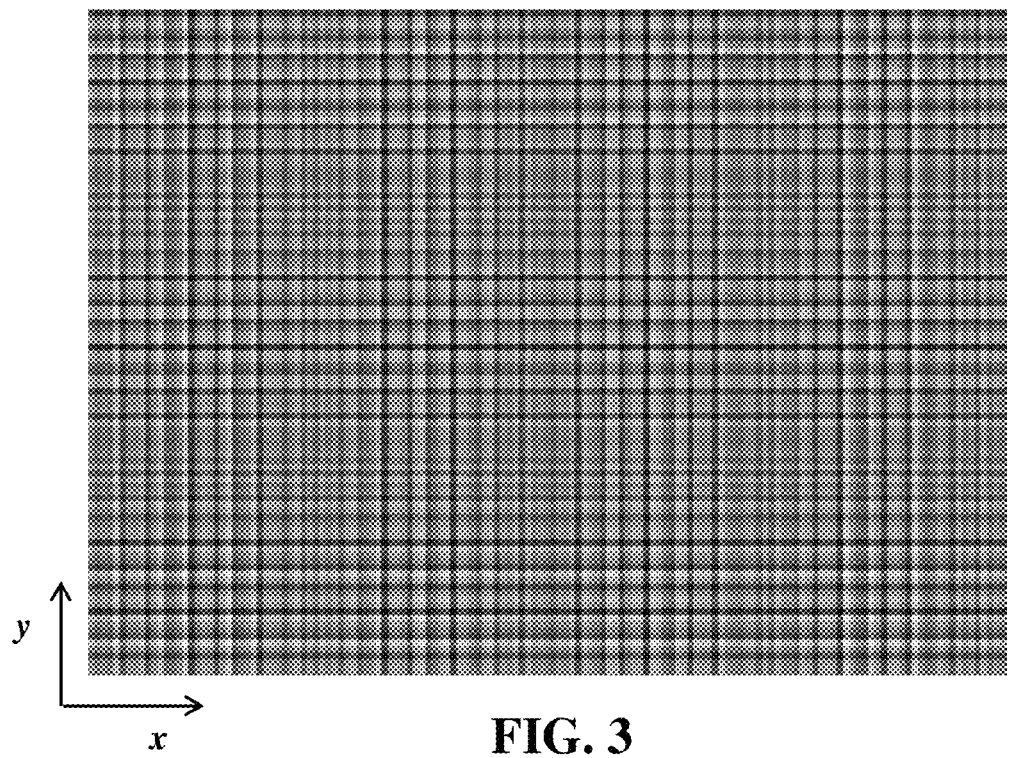
FIG. 3 is a schematic view of a three-frequency pattern which may be employed in one embodiment of the optical inspection system.

As required, detailed embodiments of the present invention are disclosed herein. However, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Referring to FIG. 1, a glass sheet optical inspection system, generally indicated as 10, is disclosed and includes a conveyor 12 which conveys the glass sheet G in a first direction generally parallel to a first dimension of the glass sheet. In the depicted embodiment, the contoured glass sheet G is a generally rectangular vehicle windshield or backlight, having a first dimension which is the relatively smaller dimension (and which may alternatively be referred to as the height) and a second, relatively larger dimension (which may alternatively be referred to as the width). The glass sheet G is curved about one or more axes of curvature that are generally parallel to the first direction. The conveyor 12 may be a single conveyor dedicated solely to transporting the glass sheet G through the optical inspection system 10 which may be configured and/or operated as a stand-alone optical inspection system. Alternatively, the conveyor 12 may be one of a series of conveyors which convey the glass sheet through a variety of process stations, such as, for example, heating, forming, and annealing or tempering stations found in a typical automotive, architectural and/or solar glass sheet fabrication systems.

The optical inspection system 10 depicted in FIGS. 1 and 2 also includes two or more displays 14-24. Each display projects a contrasting pattern, such as, for example, those patterns shown in FIGS. 4 and 5, which pattern is projected onto the surface of the glass sheet as it is conveyed beneath the screens. The depicted system 10 also includes two or more cameras 28-40. Each one of the cameras 28-40 is uniquely paired with one of each of the corresponding number of displays 14-26. In the depicted embodiment of the system 10, an aperture is formed in the center of each of the displays 14-26. The camera associated with a particular display is mounted such that the viewing aperture of the camera extends through the aperture in its associated display such that the principal viewing access of the camera is perpendicular to the surface the screen. It will, of course, be appreciated by those skilled in the art that each camera may be alternatively arranged at other locations with respect to its associated display, so long as the camera is positioned to detect the reflected image of the pattern projected on the surface of the glass sheet from that display, and not detect reflected images of patterns projected from other displays in its field of view.

Referring still to FIGS. 1 and 2, the number and placement of the displays is dependent upon the size of the displays, as well as the width and the curvature of the glass sheet. In the depicted embodiment of the system 10, the camera/display pairs are positioned such that the principal viewing axis of each camera is generally perpendicular to the surface of the glass sheet. The total number of camera/display pairs must be sufficient such that the total number of projected patterns span the entire width of the surface of the glass sheet part to be analyzed.

Referring again to FIG. 1, the optical inspection system 10 also includes a programmable control, depicted in this embodiment as a computer 42, which includes at least one processor programmed to detect the glass sheet as it advances on the conveyor, control each of the cameras 28-40 to acquire one or more images of the pattern reflected off the surface of the glass sheet as it is conveyed below the cameras/displays, construct the definition of the glass sheet surface, and perform the desired optical distortion analysis (using, for example, the technique depicted and described in FIGS. 7-9, and as further described hereinafter). In any embodiments of the system 10 (such as the embodiment depicted in the Figures) where the field of view of a camera in any width zone is smaller than the first dimension (height) of the glass sheet, the system control may be programmed to acquire multiple images as the glass is conveyed in the first direction. It will be appreciated that the number of images acquire by each camera should be sufficient that the surface information developed from each image (as hereinafter described) can be combined to form a description of the entire surface across the height (i.e., in the direction of conveyance) of the glass sheet.

Where, as in the depicted embodiment, the cameras are mounted with their viewing aperture extending through an aperture in the display, the system control 42 may be programmed to acquire multiple images as the glass is conveyed in the first direction to insure that an image of the reflected pattern is obtained in a previous or subsequent image of the moving sheet for that portion of the surface of the glass sheet that, in any one of the captured images, is in the area of reflection of the display aperture. Again, it will be appreciated that the number of images acquire by each camera should also be sufficient that the surface information developed from each image (as hereinafter described) can be combined to form a description of the entire surface across the height in the area in which a single image might include an image of the display aperture rather than the reflected pattern.

The surface descriptions for each of the cameras are similarly combined to form a description of the entire surface across the width (or across the area of interest in the direction of the width) of the glass sheet.

Referring to FIG. 3, in one embodiment the screen pattern is a three-frequency pattern constructed by superimposition of three different frequency sinusoidal patterns in each of the x and y directions of the coordinate system employed by the system logic. It should be noted that, in the illustrated embodiment, the x-y coordinate system axes are chosen to be oriented such that they are coincident with the x and y axes of the display (and, as well, the y axis is parallel to the direction of travel of the conveyor and the x axis is orthogonal to the direction of travel of the conveyor).

The sinusoidal patterns are chosen and combined to insure that the portion of the resultant pattern appearing on the display is non-repetitive, thereby ensuring that, for the image data collected, each pixel in the camera's field of view will correspond uniquely to a single point on the display. Each of the three frequencies may be relatively prime values, and are selected such that they are spaced apart within the envelope of frequencies bound by the minimum and maximum frequency limits of the camera's optics.

The image of this three-frequency pattern reflected from the surface of the glass sheet may then be mathematically deconstructed into three single frequency images in each of the x and y direction. Phase information corresponding to each of the three frequencies can then be isolated and utilized as hereinafter described to develop an accurate description of the glass sheet surface.

Figure 4:
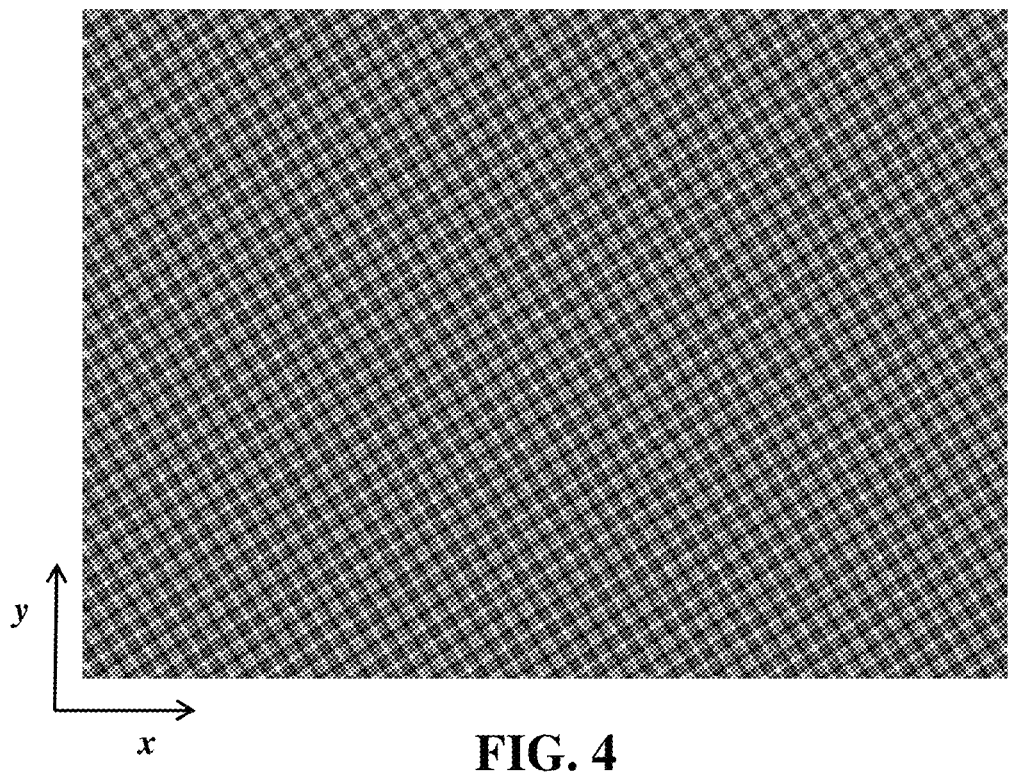
FIG. 4 is a schematic view of a two-frequency pattern which may be employed in another embodiment of the optical inspection system.

In another embodiment, illustrated in FIG. 4, a two-frequency pattern may be utilized. This two-frequency pattern may be constructed by superimposition of two different frequency sinusoidal patterns in each of two orthogonal directions which are rotated (or skewed) about the axes that are used to separate the analysis into orthogonal components, such that each of the sinusoidal components of the pattern yields phase information in both the x and y directions. In the illustrated embodiment, the x, y coordinate system axes that are used by the system logic to separate the analysis into orthogonal components are coincident with the x and y axes of the display (and the y axis is as well, coincident with the direction of conveyance).

Thus, in the illustrated embodiment, the orthogonal directions of the sinusoidal patterns are skewed from the x and y axes of the display. It will be appreciated, however, that any other convenient orientation may be chosen for the axes that are used by the system to separate the analysis into orthogonal components, so long as the sinusoidal patterns are rotated about the axes that are used to separate the analysis into orthogonal components to yield phase information in both the x and y directions.

Again, the sinusoidal patterns are chosen (relatively prime frequencies and spaced apart as described above) and combined to insure that the portion of the resultant pattern appearing on the display is non-repetitive, thereby ensuring that the image data collected that each pixel in the camera's field of view will correspond uniquely to a single point on the display.

The image of this two-frequency pattern reflected from the surface of the glass sheet may then be similarly mathematically deconstructed. Again, phase information corresponding to each of the two frequencies can be isolated and utilized as hereinafter described to develop an accurate description of the glass sheet surface.

It will be appreciated by those skilled in the art that, by employing a multi-frequency, non-repeating pattern and employing the deflectometry techniques hereinafter described, an accurate mathematical description of the glass sheet surface may be obtained from a single image for each point on the surface of the glass sheet from which the camera detects the reflected pattern. It is thus unnecessary to capture utilize multiple patterns, and/or multiple images, except as described herein where multiple images are acquired as the glass sheet is moved on the conveyor to construct a surface for that portion of the glass sheet that does not reflect the projected pattern in any single acquired image (e.g., (1) that portion of the glass sheet directly below the aperture in the screen, or (2) for that portion of the glass sheet that is not in the viewing area of the camera due to the fact that the height of the glass sheet is greater that the projected pattern from the screen in the direction of conveyance).

Figure 5:
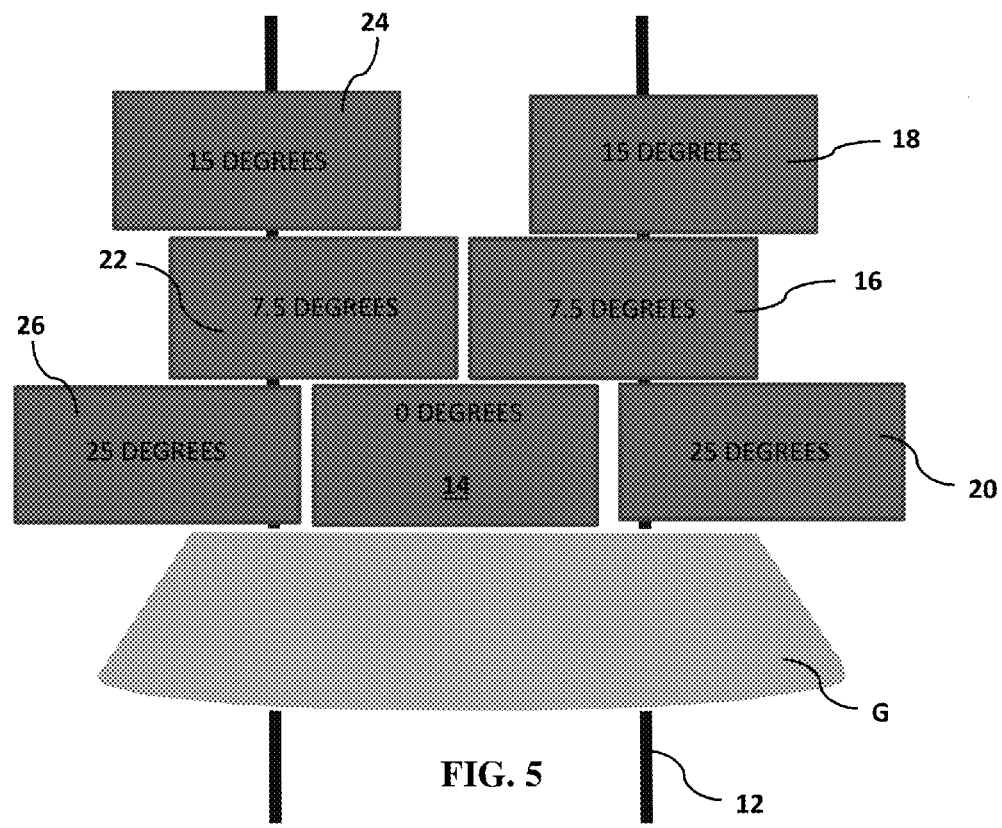
FIG. 5 is a top diagrammatic view of the arrangement of multiple display/camera pairs shown in FIG. 2 including the angular orientation of the displays/cameras for a particular glass part.
Figure 6:
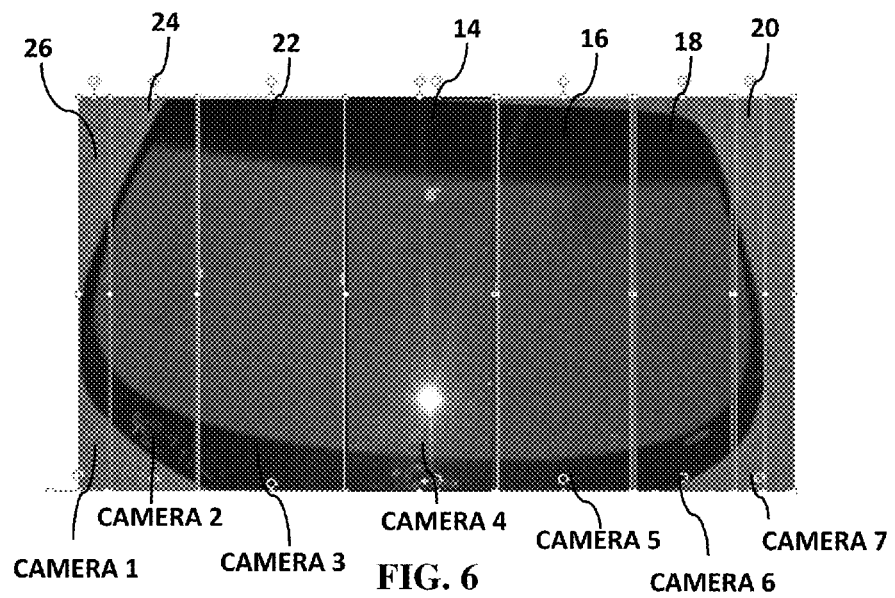
FIG. 6 is a top view of a particular curved glass sheet illustrating the areas of the glass sheet surface analyzed by each of the display/camera pairs utilized in the system of FIG. 1.

Referring now to FIGS. 5 and 6, in the illustrated embodiment, and for the depicted glass sheet part G, the second dimension (width) of the glass sheet was divided into seven zones. These zones were identified as required due to the dimension of display pattern viewed by the camera, and the width dimension and curvature of the particular glass sheet part. In this example, first zone display 20 is oriented at an angle of about 25° counterclockwise from horizontal (when viewed as in FIG. 1), display 18 is angled at about 15° counterclockwise, display 16 is angled at about 7.5° counterclockwise, display 14 is approximately horizontal, display 22 is angled at approximately 7.5° clockwise from horizontal, display 24 is angled at about 15° clockwise, and display 26 is angled at about 25° clockwise. In the illustrated embodiment, the seven displays 14-26 are arranged in in the direction of conveyance of the glass sheet G. However, as will be appreciated by those skilled in the art, other arrangements may be optimal for glass sheet parts of different widths and curvatures, provided that the screens are arranged such that each associated camera detects only the reflected pattern from its associated display in its field of view, and the surface areas detected by all cameras together comprise the surface across the entire width of the glass sheet part.

The glass sheet optical inspection system 10 includes a surface data acquisition system which employs the above-described camera and display pairs and acquired images, as well as logic for developing an accurate three-dimensional description of the surface from the reflected patterns from each image, and logic for combining the surface descriptions developed from the images as hereinafter described to obtain an accurate mathematical description of the entire surface of the glass sheet.

The glass sheet optical inspection system 10 may also, in addition to the surface data acquisition system, include one or more computers and/or programmable controls including logic for processing the acquired surface data to analyze the optical characteristics of the glass sheet.

Figure 10:
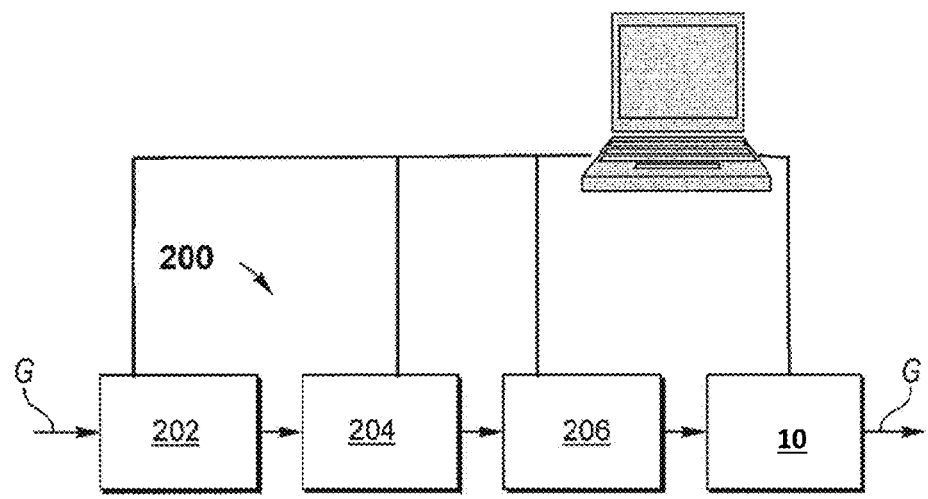
FIG. 10 is a schematic diagram of one embodiment of the disclosed optical inspection system installed in-line in a typical automotive glass forming and tempering line.
Figure 11:
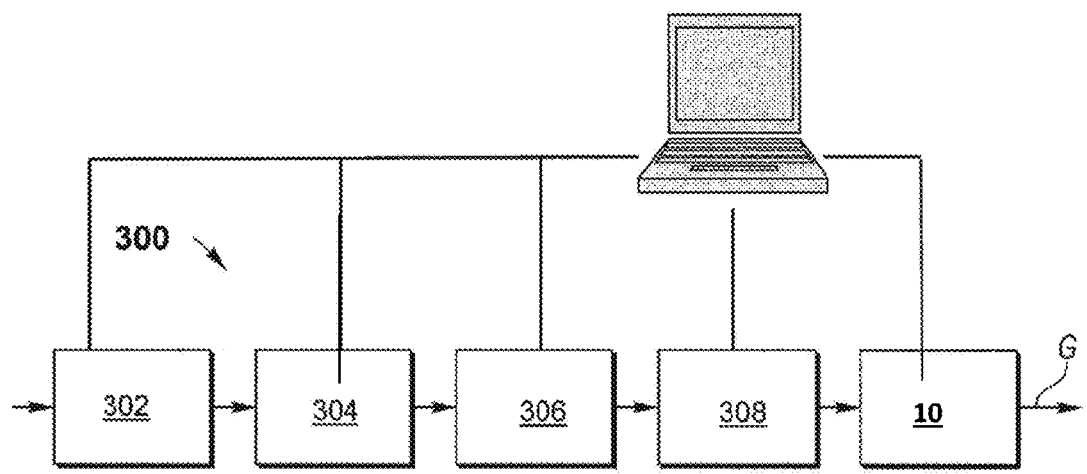
FIG. 11 is a schematic diagram of another embodiment of the disclosed optical inspection system installed in-line in a typical automotive windshield forming line.

The optical inspection system 10 may, in turn, be incorporated into a system for fabricating glass sheets including one or more processing stations and one or more conveyors for conveying the glass sheets from station to station during processing, such as fabrication systems 200 and 300 schematically shown in FIGS. 10 and 11.

Figure 7:
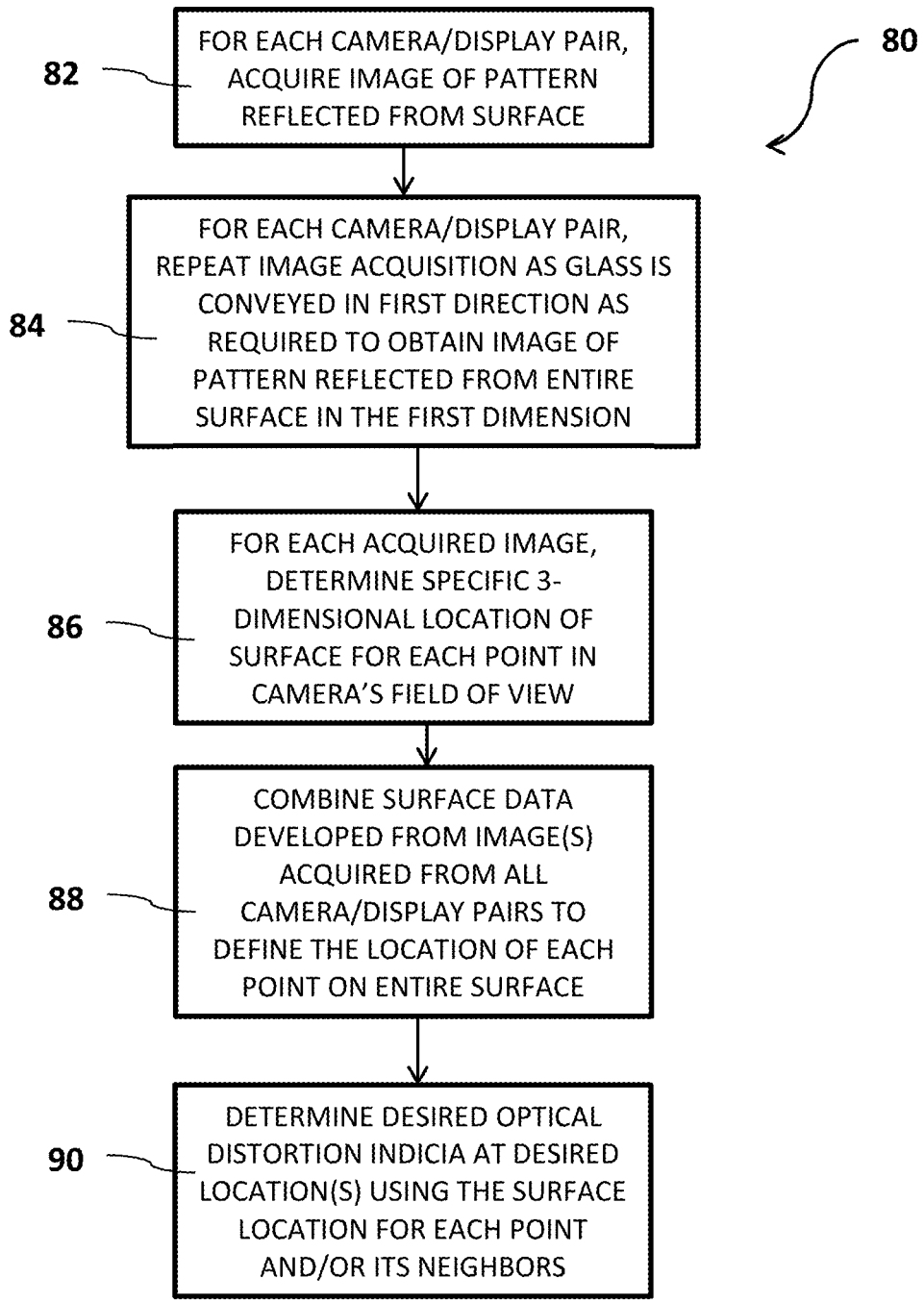
FIG. 7 is a flow chart describing the logic employed in one embodiment of the disclosed optical inspection system.

FIG. 7 describes the method 80 performed by the control logic of the disclosed optical inspection system 10. When the system 10 determines that a glass sheet is in the appropriate position on the conveyor, the system activates the appropriate camera(s), at 82, to acquire an image of the pattern reflected from the surface of the glass sheet. The position of the glass sheets can be determined using conventional sensors.

As indicated at 84, one or more additional images may be obtained from each camera, as required, as the glass sheet moves on the conveyor. As previously described, the number of images acquired by each camera is determined by at least two considerations. First, in embodiments of the system wherein the cameras are mounted within an aperture of their associated displays, a sufficient number of images must be acquired to ensure that the system acquires a reflected image of the pattern for all of the points in the viewing area, including those points from which the display pattern is not reflected in a particular image due to the fact that it is located within the area that includes a reflection of the aperture. Second, multiple images may be required as the glass is conveyed across the viewing area of the camera in embodiments of the system where the field of view of the camera is not large enough to acquire a reflection of the display pattern from the surface of the glass sheet across its entire first dimension (i.e., the entire height) in one image.

For each of the acquired images, the system, at 86, must determine the precise location in three-space of each point on the surface of the glass sheet based upon the reflected pattern in the image. As previously described, the use of a pattern which is non-repeating in the camera's viewing area ensures that each point on the display screen that is reflected within the viewing area of the camera will be uniquely associated with a pixel that detects the reflected pattern.

Conventional image processing techniques may be employed to determine the x and y locations (i.e., in the focal plane of the camera) for each point on the surface of the glass sheet that is in the viewing area of the camera for that image. Other known processing techniques may be employed to determine the z location (a.k.a. the elevation) of each point. In the disclosed embodiment, a mapping vector technique is employed (as depicted in FIGS. 8 and 9, and as more fully described hereinafter) to determine the elevation of each single point on the surface of the glass from the image of the reflected projected pattern.

In one embodiment, the x, y, and z values developed for each point in the viewing area of a particular camera are typically developed in a coordinate system associated with that camera. In one embodiment, for example, the origin of the coordinate system for each camera is set at that camera's origin 98 (as shown in FIG. 8). The resulting collection of points associated with the surface in the viewing area of each camera ("the point cloud") may then be combined for each image collected by that camera.

The system, at 88, then combines the developed surface data for each of the images acquired from all of the cameras to obtain the surface definition which identifies the location of each point in three-space for the entire surface of the glass sheet. In one embodiment, the point clouds for each camera are converted to a common ("global") coordinate system, and the point clouds are then combined to form the entire surface.

It will be appreciated that one or more other coordinate systems/origins may be selected and employed based upon a particular system's camera/display architecture and/or for computational convenience. Similarly, the combination of the surface developed from the individual acquired images may be performed using other conventional image data processing techniques.

The system then, at 90, performs one or more known optical processing techniques to determine any desired indicia of the reflective optics of the surface. For example, in one embodiment, the system 10 may be suitably programmed to analyze the developed surface to determine (1) various desired indicia of optical distortion, including the magnification and lens power, for selected portions, or for the entirety, of the surface of each glass sheet as it is transported through the system.

Figure 8:
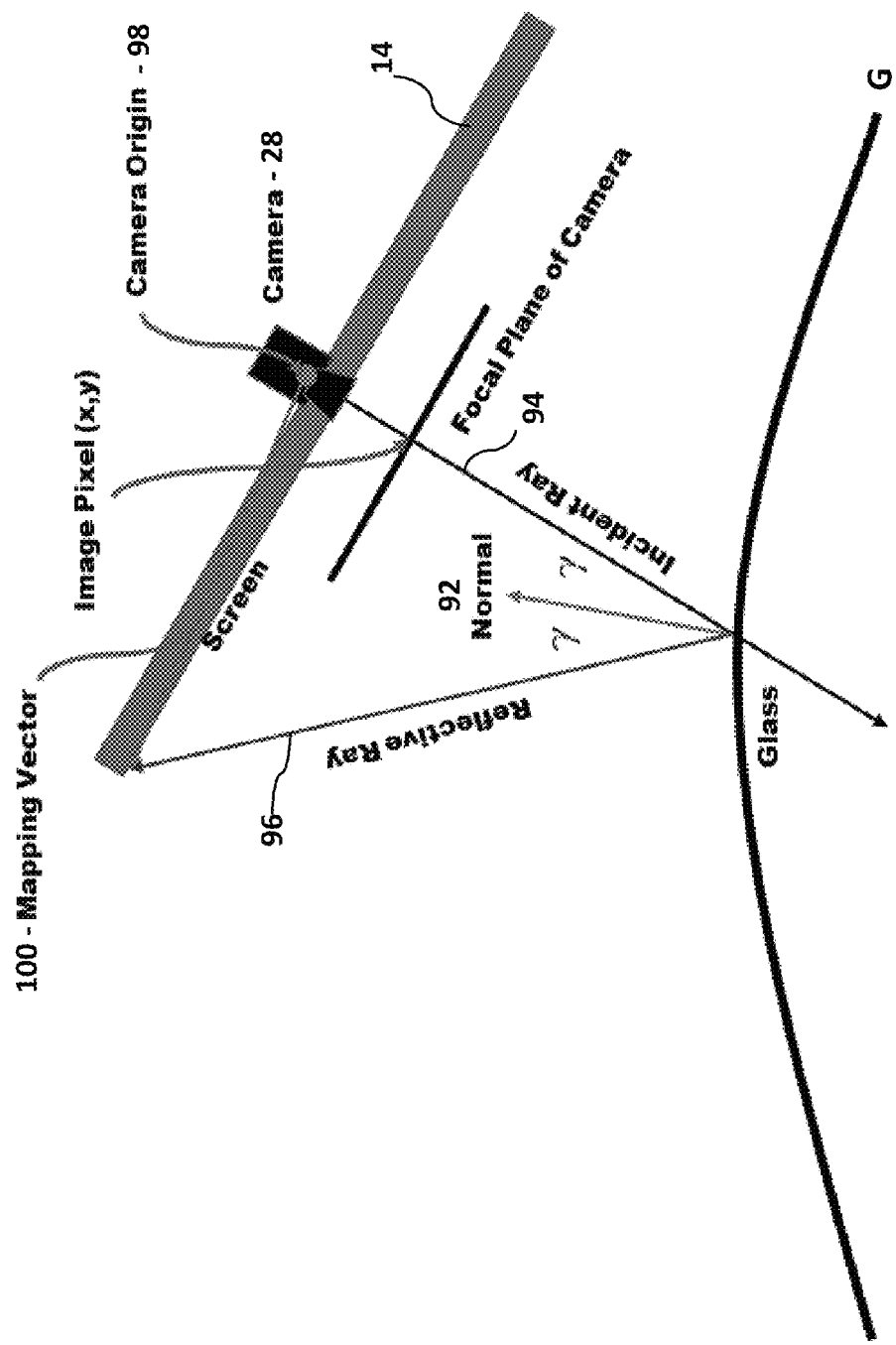
FIG. 8 is a schematic illustration of the pertinent geometric parameters that may be utilized to determine the elevation of a single point on the surface of the glass sheet according to the steps depicted in FIG. 9.
Figure 9:
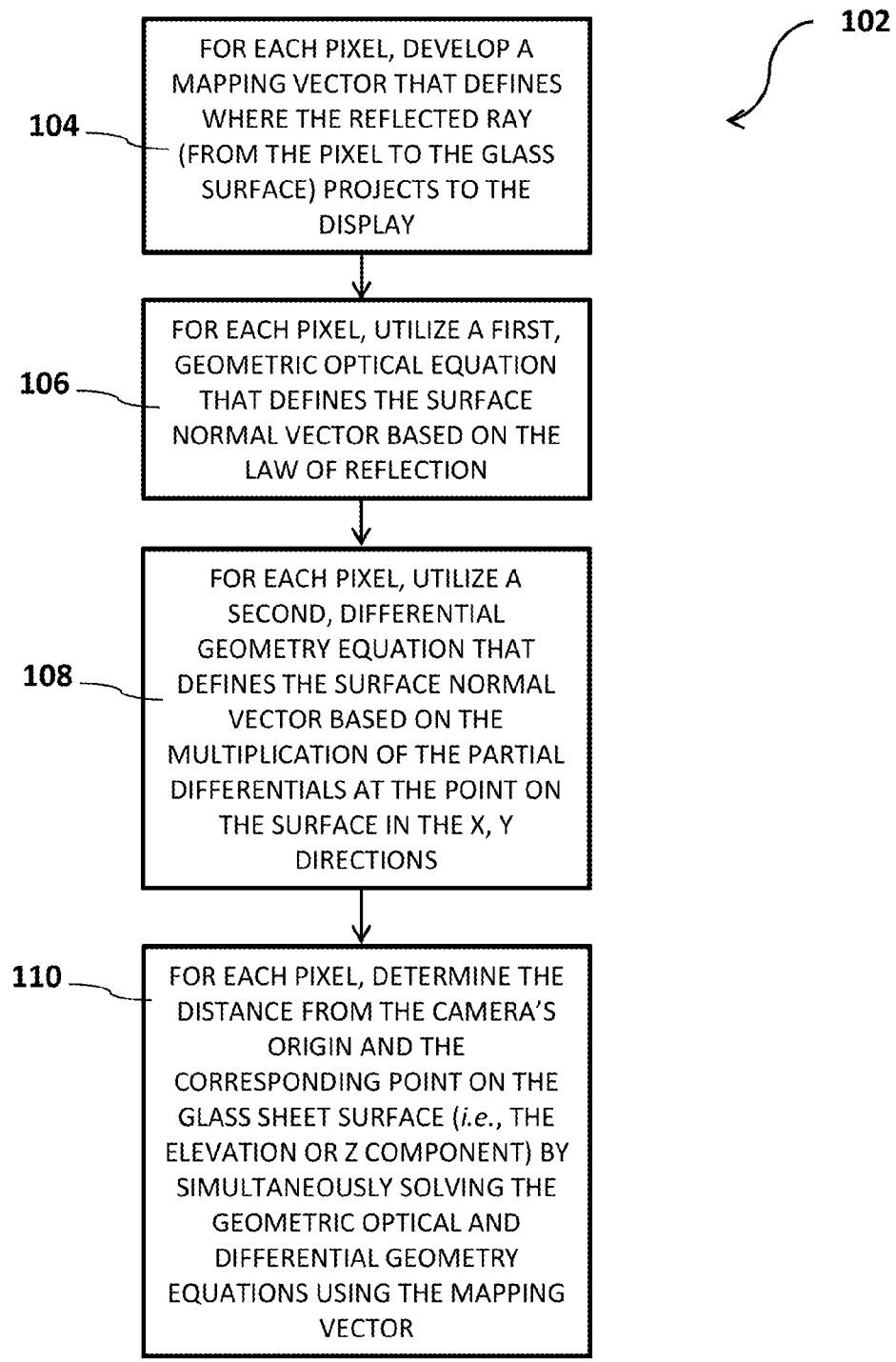
FIG. 9 is a flow chart describing the surface point resolution logic employed in one embodiment of the surface data acquisition portion of the system.

FIGS. 8 and 9 illustrate, respectively, the theoretical basis and the method performed by the control logic for determining the elevation (z value) of each point on the surface of the glass from the image of the reflected projected pattern for each acquired image. FIG. 8 illustrates the pertinent geometrical relationships between the camera 28, the display screen 14, and the surface of the glass sheet G. The three principles used to determine the elevation of a single point on the surface of the glass sheet from a reflected projected image are (1) the surface of any object can be defined by the normal vector 92 for each discrete point of the surface; (2) the law of reflection defines the normal vector 92 at each point by bisecting the angle between the incident ray 94 and the reflected ray 96 of light (also referred to herein as the "geometric optical" or "reflection angle" equation); and (3) the normal vector can also be defined by the differential geometry which describes each point on the surface of the glass sheet (also referred to herein as the "differential geometry" equation).

Referring still to FIG. 8, based upon the law of reflection, the incident ray is defined entirely by the camera intrinsics. Thus each pixel in the cameras receptor cell at the cameras origin 98 sees a point in space at varying distances through the lens. Continuing with the law of reflection, the reflected ray 96 is defined by a screen position and a surface point on the glass. The distance is constrained only where it intersects the incident ray 94. There are two mathematical expressions which define the normal vector 92. One is derived from the law of reflection. The second differential equation is derived from the geometric partial differentiation at any point on the surface. To solve the corresponding differential equations, a mapping vector 100 needs to be established, which defines, for each pixel, where the reflected ray will hit the projected pattern on the display (viewed from the camera origin). Once the mapping field (i.e., the set of mapping vectors for each pixel in the camera's field of view) is established, the distances from the camera's origin and each discrete point on the surface can be calculated.

The geometric optical equation is:

$$\vec{n} = \|\vec{v}\|\left(\vec{m} - s\frac{\vec{v}}{|\vec{v}|}\right) - \left\|\vec{m} - s\frac{\vec{v}}{|\vec{v}|}\right\|(\vec{v})$$

Where n is the surface normal, v is the camera pixel vector, m is the mapping vector, and s is the distance from the camera to the surface (along the camera vector so that the $$\left(p = s\frac{v}{|v|}\right).$$

surface point

The differential geometry describes the points on the surface of the glass sheet:

$$\vec{n} = \frac{\partial \vec{p}}{\partial x} \times \frac{\partial \vec{p}}{\partial y}$$

Since n is the cross product of the two differentials, it is by definition orthogonal to both, yielding:

$$\vec{n} \cdot \frac{\partial \vec{p}}{\partial x} = \vec{n} \cdot \frac{\partial \vec{p}}{\partial y} = 0$$

Solving these for the elevation, s:

$$\left(\|\vec{v}\|\left(\vec{m} - s\frac{\vec{v}}{|\vec{v}|}\right) - \left\|\vec{m} - s\frac{\vec{v}}{|\vec{v}|}\right\|(\vec{v})\right) \cdot \frac{\partial \vec{p}}{\partial x} = 0$$

$$\left(\|\vec{v}\|\left(\vec{m} - s\frac{\vec{v}}{|\vec{v}|}\right) - \left\|\vec{m} - s\frac{\vec{v}}{|\vec{v}|}\right\|(\vec{v})\right) \cdot \frac{\partial \vec{p}}{\partial y} = 0$$

FIG. 9 illustrates how a suitably programmed computer could implement this mapping vector technique 102. At 104 the system develops a mapping vector that defines where the reflected ray projects to the display (again, viewed mathematically from the camera origin). A first expression, the geometric optical equation, at 106, defines the surface normal vector for each point on the glass sheet surface within the camera's viewing area based upon the law of reflection. A second equation, the differential geometry equation, at 108, defines the surface normal vector-based on the multiplication of the partial differentials which describe the point on the surface in the x, y directions. These two equations may be solved simultaneously using the mapping vector to obtain the elevation, s (that is, the z distance—the distance between the glass surface and the camera origin) for each point on the glass sheet surface that is within the viewing area of the camera. This information, coupled with the previously developed x and y locations of each surface point, yields a specific description, in x, y, and z, for each point on the surface.

It will be appreciated by those skilled in the art that other known methods may be utilized to develop unambiguous locations in three dimensions for each of the points on the surface of the glass sheet based upon the unambiguous x and y locations of the reflected patterns at each pixel location of the image, and the geometrical relationship between the focal plane of the camera, the display screen, and the glass sheet. However, it has been determined that the elevation of each point on the surface of the glass sheet can be quickly determined using the principles described above and illustrated in FIG. 8, and the technique described above and illustrated in FIG. 9, without resorting to projecting multiple, varying patterns and/or analyzing multiple images of the same viewing area to thereby determine a three-dimensional definition of the glass surface.

Referring again to FIGS. 1 and 2, the disclosed glass sheet optical inspection system 10 may be mounted in-line to inspect glass sheets as they are transported on a conveyor associated with a glass sheet processing system which performs multiple fabricating operations on the glass sheets. The disclosed system 10 includes a surface data acquisition system and a computer including logic for receiving the captured image data, developing a three-dimension description of the glass sheet surface from the image data, performing one or more optical processing operations to analyze the optical characteristics of the glass sheet and displaying or otherwise reporting selected information associated with the optical analysis. As previously described, computer 42 may be operably connected to the conveyor and cameras to perform the image acquisition, the surface development, and the optical processing described herein. Alternatively, computer 42 may be combined with one or more other computers and/or programmable controls to perform these functions.

The system 10 may also be programmed by the user to graphically and numerically display various indicia of optical distortion, including those indicia most relevant to industry standards, or other indicia considered relevant in the industry to the analysis of the optical reflection quality of formed and fabricated glass sheets.

The digital cameras 28-40 are each connected via a conventional data line to one or more computers, such as computer 42, which may be suitably programmed to acquire the digital image data from the camera, process the image data to obtain the desired surface definition for the glass sheet, and analyze the data to develop various indicia of distortion. The computer 42 may also be programmed to present the derived image distortion information in both graphical (e.g., color-coded images) and statistical forms. If desired, various other statistical data can be derived and reported for predefined areas of the glass sheet, including the maximum, minimum, range, mean, and standard deviation in lens power, or other indices of distortion which may be of interest.

As will be appreciated by those skilled in the art, the optical inspection system 10 may additionally or alternatively employ other known image processing techniques to collect and analyze the acquired image data, develop a definition of the surface, and provide various indicia of the reflected optical characteristics for each glass sheet.

In one embodiment, the displays 14-26 are light boxes that utilize conventional lighting (such as fluorescent lights) behind a translucent panel upon which the contrasting pattern is printed, painted, or otherwise applied using conventional methods. The digital cameras 28-40 are connected to the computer 60 using known methods, preferably so that the acquisition of the image by the camera may be controlled by the computer 42.

FIG. 11 illustrates a typical glass sheet heating, bending, and tempering system 200 which includes the in-line optical inspection system 10, as well as the surface data acquisition system, of the present invention. In this installation, the glass sheets (indicated as G) enter a heating zone 202 where the glass is softened to a temperature suitable for forming the glass into the desired shape. The heated glass sheet is then conveyed to a bending station 204 where the softened sheet is formed to the desired shape, and thereafter further conveyed to a cooling station 206 where the glass sheet is cooled in a controlled manner to achieve the appropriate physical characteristics. In this embodiment, the glass sheet would then be conveyed out of the cooling station onto a conveyor from which the sheet is conveyed for image acquisition and analysis by the disclosed optical inspection system 10. Following the measurement, the glass sheet would be moved on the conveyor 12 for further processing. It will be appreciated that the transport and conveyance of the glass can be achieved by using known techniques such as by roller, air-float, or belt conveyors, positioners, and robotic arms, in order to handle the glass in the manner described. It will also be appreciated that a plurality of conveyors, each of which may be independently controlled to move the glass sheets through the different processing stations at speeds to efficiently govern the flow and processing of the glass sheets throughout the system 200.

FIG. 12 similarly schematically illustrates an in-line optical inspection system 10 and the associated surface data acquisition system of the present invention in a typical automotive windshield fabrication system 300, which may include a heating station 302, a bending station 304, a cooling station 306, and a lamination station 308, upstream of the optical inspection system 10.

Selected data output by the disclosed in-line optical inspection system 10 may also be provided as input to the control logic for the associated glass sheet heating, bending, and tempering system 200 (or automotive windshield fabrication system 300) to allow the control(s) associated with one or more of the stations the glass sheet system to modify its (their) operating parameters as a function of the optical data developed from previously processed glass sheets.

It will be appreciated that the optical inspection system 10 of the present invention could alternatively be mounted in-line at various other points in the above-described and other glass sheet fabrication systems as desired to maximize the production rate of the system, so long as the optical distortion measurements are taken after the glass sheet has been formed to its final shape.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for measuring the optical characteristics of a curved glass sheet, the glass sheet having a first dimension and a second dimension, wherein the glass sheet is curved at least about one or more axes of curvature which are generally parallel to the first dimension, the apparatus comprising:
   a conveyor for conveying the glass sheet in a first direction generally parallel to the first dimension of the glass sheet;
   at least two displays, each display projecting a preselected contrasting pattern,
   at least two cameras, each one of the at least two cameras being uniquely paired with one of the displays, wherein each display and camera pair are mounted in a spaced-apart relationship a known distance and angle from the surface of the glass sheet such that the camera detects the reflected image of the pattern projected on the surface of the glass sheet from its associated display, and wherein each of the display and camera pairs are spaced apart from each other at least in a second direction across the second dimension of the glass sheet such that each camera detects the reflected image of the pattern projected on the surface of the glass sheet from only its associated display, and wherein the patterns detected by the cameras together cover the entire surface in the direction of the second dimension of the glass sheet; and
   a programmable control including at least one processor programmed to execute logic for controlling each of the cameras to acquire at least one image of the reflected pattern of the associated display on the glass sheet as the glass sheet is conveyed across the path of the projected pattern in the first direction, logic for analyzing and combining the data acquired by the cameras to construct surface data representative of the surface of the glass sheet, and logic for analyzing the data representative of the surface of the glass sheet to determine optical characteristics of the glass sheet.

2. The system of claim 1 wherein the first dimension is the minor dimension of the glass sheet and the second dimension is the major dimension of the glass sheet.

3. The system of claim 1 wherein the logic for analyzing and combining the data acquired by the cameras to construct surface data representative of the surface of the glass sheet includes logic for constructing surface data representative of the entire surface across the second dimension of the glass sheet.

4. The system of claim 1 wherein a single image of the reflected patterns projected by the displays from each of the associated cameras cannot be combined to define data representative of the surface of the glass sheet across the entire second dimension of the glass sheet, and wherein the programmable control includes at least one processor programmed to execute logic for controlling each of the cameras to acquire multiple images of the reflected pattern of the associated display on the glass sheet as the glass sheet is conveyed across the path of the projected pattern in the first direction, and logic for analyzing and combining the data acquired by the multiple images acquired by each camera to construct surface data representative of the surface of the glass sheet across the entire first dimension of the glass sheet.

5. The system of claim 1 wherein each display includes an aperture, and wherein the associated camera is mounted behind its associated display such that the principal axis of the camera is generally normal to the surface of the display and the image is received by the camera through the aperture, and wherein the programmable control includes logic for controlling each of the cameras to acquire multiple images of the reflected pattern of the associated display on the glass sheet as the glass sheet is conveyed in the first direction for at least a distance greater than the size of the aperture, and logic for analyzing and combining the data from the multiple images to define data representative of the surface of the glass sheet in the area for which any one of the acquired images includes a reflected image of the aperture.

6. The system of claim 1 wherein the logic for analyzing and combining the data acquired by the cameras to construct surface data representative of the surface of the glass sheet includes at least:
   logic for developing, for each pixel in in the viewing area of the camera for each acquired image, a mapping vector that defines where the reflected ray projects from the camera origin to the associated display; and
   logic for developing, for each pixel in the viewing area of the camera for each acquired image, the elevation value, s, of the point, by simultaneously solving (1) the geometric optical equation and (2) the differential geometry equation, using the mapping vector.

7. The system of claim 1 wherein the preselected contrasting pattern is non-repeating over the entire viewing area of the camera.

8. The system of claim 1 wherein the preselected contrasting pattern is a three-frequency pattern, constructed by superimposition of three different frequency sinusoidal patterns in each of the x and y directions of the coordinate system employed by the system logic.

9. The system of claim 8 wherein the preselected contrasting pattern is a two-frequency pattern, constructed by superimposition of two different frequency sinusoidal patterns in each of the x and y directions of the pattern, where the two different frequency sinusoidal patterns are rotated with respect to the axes of the coordinate system employed by the system logic.

10. The system of claim 1 wherein the logic for analyzing the data representative of the surface of the glass sheet to determine optical characteristics of the glass sheet includes logic for determining selected indicia of optical distortion associated with each point of interest on the surface of the glass sheet.

11. The system of claim 10 wherein the selected indicia of distortion includes lens power.

12. The system of claim 1 wherein the system is incorporated into a system for fabricating curved glass sheets including multiple processing stations and one or more conveyors for conveying the glass sheet from station to station during processing.

13. A system for fabricating curved glass sheets including one or more processing stations and one or more conveyors for conveying the glass sheet from station to station during processing, one of the processing stations including an apparatus for measuring the optical characteristics of a glass sheet as the glass sheet is conveyed in a first direction generally parallel to the first dimension of the glass sheet, the apparatus comprising;
   at least two displays, each display projecting a preselected contrasting pattern,
   at least two cameras, each one of the cameras being uniquely paired with one of the displays, wherein each display and camera pair are mounted in a spaced-apart relationship a known distance and angle from the surface of the glass sheet such that the camera detects the reflected image of the pattern projected on the surface of the glass sheet from its associated display, and wherein each of the display and camera pairs are spaced apart from each other at least in a second direction across the second dimension of the glass sheet such that each camera detects the reflected image of the pattern projected on the surface of the glass sheet from only its associated display, and wherein the patterns detected by the cameras together cover the entire surface in the direction of the second dimension of the glass sheet; and a programmable control including at least one processor programmed to execute logic for controlling each of the cameras to acquire at least one image of the reflected pattern of the associated display on the glass sheet as the glass sheet is conveyed across the path of the projected pattern in the first direction, logic for analyzing and combining the data acquired by the cameras to construct surface data representative of the surface of the glass sheet, and logic for analyzing the data representative of the surface of the glass sheet to determine optical characteristics of the glass sheet.

14. The system of claim 13 wherein the first dimension is the minor dimension of the glass sheet and the second dimension is the major dimension of the glass sheet.

15. The system of claim 13 wherein the logic for analyzing and combining the data acquired by the cameras to construct surface data representative of the surface of the glass sheet includes logic for constructing surface data representative of the entire surface across the second dimension of the glass sheet.

16. The system of claim 13 wherein a single image of the reflected patterns projected by the displays from each of the associated cameras cannot be combined to define data representative of the surface of the glass sheet across the entire second dimension of the glass sheet, and wherein the programmable control includes at least one processor programmed to execute logic for controlling each of the cameras to acquire multiple images of the reflected pattern of the associated display on the glass sheet as the glass sheet is conveyed across the path of the projected pattern in the first direction, and logic for analyzing and combining the data acquired by the multiple images acquired by each camera to construct surface data representative of the surface of the glass sheet across the entire first dimension of the glass sheet.

17. The system of claim 13 wherein each display includes an aperture, and wherein the associated camera is mounted behind its associated display such that the principal axis of the camera is generally normal to the surface of the display and the image is received by the camera through the aperture, and wherein the programmable control includes logic for controlling each of the cameras to acquire multiple images of the reflected pattern of the associated display on the glass sheet as the glass sheet is conveyed in the first direction for at least a distance greater than the size of the aperture, and logic for analyzing and combining the data from the multiple images to define data representative of the surface of the glass sheet in the area for which any one of the acquired images includes a reflected image of the aperture.

18. The system of claim 13 wherein the logic for analyzing and combining the data acquired by the cameras to construct surface data representative of the surface of the glass sheet includes at least:

logic for developing, for each pixel in in the viewing area of the camera for each acquired image, a mapping vector that defines where the reflected ray projects from the camera origin to the associated display; and logic for developing, for each pixel in the viewing area of the camera for each acquired image, the elevation value, s, of the point, by simultaneously solving (1) the geometric optical equation and (2) the differential geometry equation, using the mapping vector.

19. The system of claim 13 wherein the logic for analyzing the data representative of the surface of the glass sheet to determine optical characteristics of the glass sheet includes logic for determining selected indicia of optical distortion associated with each point of interest on the surface of the glass sheet.

20. The system of claim 19 wherein the selected indicia of distortion includes lens power.

21. The system of claim 13 wherein the one or more processing stations include a heating station for heating the glass sheet to a temperature adequate to soften the glass for forming into a desired shape, a bending station wherein the softened sheet is formed to the desired shape, and a cooling station wherein the formed glass sheet is cooled in a controlled manner.

22. A system for measuring the optical characteristics of a curved glass sheet, the glass sheet having a first dimension and a second dimension, wherein the glass sheet is curved at least about one or more axes of curvature which are generally parallel to the first dimension, the apparatus comprising:

a conveyor for conveying the glass sheet in a first direction generally parallel to the first dimension of the glass sheet;

a display projecting a preselected contrasting pattern on the surface of the glass sheet, a camera mounted in a spaced-apart relationship a known distance and angle from the surface of the glass sheet such that the camera detects the reflected image of the pattern projected on the surface of the glass sheet from the display, and wherein the pattern detected by the camera covers the entire portion of interest on the surface in the direction of the second dimension of the glass sheet; and a programmable control including at least one processor programmed to execute logic for controlling the camera to acquire at least one image of the reflected pattern of the associated display on the glass sheet as the glass sheet is conveyed across the path of the projected pattern in the first direction, logic for analyzing and combining the data acquired by the camera to construct surface data representative of the surface of the glass sheet, and logic for analyzing the data representative of the surface of the glass sheet to determine optical characteristics of the glass sheet; and wherein the logic for analyzing and combining the data acquired by the camera to construct surface data representative of the surface of the glass sheet includes at least:

logic for developing, for each pixel in in the viewing area of the camera for each acquired image, a mapping vector that defines where the reflected ray projects from the camera origin to the associated display; and logic for developing, for each pixel in the viewing area of the camera for each acquired image, the elevation value, s, of the point, by simultaneously solving (1) the geometric optical equation and (2) the differential geometry equation, using the mapping vector.

* * * * *